(12) United States Patent
Cox et al.

(10) Patent No.: US 6,802,605 B2
(45) Date of Patent: Oct. 12, 2004

(54) CONTACT LENS AND METHOD FOR FITTING AND DESIGN

(75) Inventors: Ian G. Cox, Honeoye Falls, NY (US); Michele Lagana, Honeoye Falls, NY (US)

(73) Assignee: Bausch and Lomb, Inc., Rochester, NY (US)

(*) Notice: Subject to any disclaimer, the term of this patent is extended or adjusted under 35 U.S.C. 154(b) by 111 days.

(21) Appl. No.: 10/013,987

(22) Filed: Dec. 11, 2001

(65) Prior Publication Data

US 2003/0107703 A1 Jun. 12, 2003

(51) Int. Cl.[7] .............................................. G02C 7/04
(52) U.S. Cl. ............................. 351/160 R; 351/160 H; 351/161; 351/177
(58) Field of Search ..................... 351/160 R, 160 H, 351/161, 162, 177

(56) References Cited

U.S. PATENT DOCUMENTS

| | | | |
|---|---|---|---|
| 6,176,580 B1 | 1/2001 | Roffman et al. | 351/177 |
| 6,270,221 B1 * | 8/2001 | Liang et al. | 351/221 |
| 6,499,843 B1 * | 12/2002 | Cox et al. | 351/246 |

* cited by examiner

Primary Examiner—Scott J. Sugarman

(57) ABSTRACT

Wavefront aberration measurements measured in response to design parameter changes in a contact lens, for example, are used to design and prescribe contact lenses offering improved vision quality. In-situ optical performance of trial lenses provides real-time, objectively determined data as a design model for the lenses. Lenses designed by the inventive process are described as well as a method for using an aberrometer to design and prescribe contact lenses.

34 Claims, 3 Drawing Sheets

CONTACT LENS AND METHOD FOR FITTING AND DESIGN

BACKGROUND OF THE INVENTION

1. Field of the Invention

The present invention relates to contact lenses. In particular, the invention provides a method for designing a contact lens, prescribing a contact lens based upon the design method, the use of a wavefront sensor to carry out such methods, and contact lenses obtained by these methods.

2. Description of Related Art

Contact lenses come in many forms: soft, RGP, monofocal, multifocal, diffractive, alternating style, simultaneous style, and more. They provide correction for various vision problems including myopia, hyperopia, astigmatism, presbyopia, and others.

Typical contact lens design involves designing the lens' physical parameters, such as posterior surface curvature over the optical and transition zones, anterior surface curvature, surface shapes, thickness, and others, based on the need for each parameter to fit the cornea in an appropriate fashion, namely, to center over the pupil, to move appropriately with blinking, to provide an acceptable level of comfort to the wearer, and to provide the necessary optical correction of vision. These parameters, particularly surface curvatures, are usually derived by a combination of experience or historical data gathered from the performance of previous designs, and empirical "trial" fittings and testing of the new design on a sample of intended patients. Based upon the subjective response of the patients and observations by the fitter, the design may be altered to achieve the intended outcome.

In consideration of the foregoing, the inventors have recognized a need for, and advantages resulting from, an improved method for designing contact lenses based upon objective criteria, and for providing contact lenses based upon the improved design. The inventive methods allow the design parameters of the lens to be chosen which provide an optimized optical correction. Lenses provided according to the invention will result in better optical performance in-situ, encompassing the effects created by placing the lens on the eye.

SUMMARY OF THE INVENTION

An embodiment of the invention is directed to an improved method for designing a contact lens. An aspect of this embodiment involves the steps of determining an objective measurement criteria of optical performance of a contact lens in-situ, determining a technique for measuring this criteria, determining a lens design parameter (for a constant refracting power) that can be varied to induce a change in the optical performance of the lens in-situ, measuring the in-situ optical performance of a test lens over a range of different design parameter values, and selecting the design parameter value for designing a contact lens that gives a desired in-situ optical performance measurement. Objective, in-situ optical performance is preferably determined by a retinal image metric such as, e.g., the point spread function (PSF), modulation transfer function (MTF), Strehl ratio, and others well understood in the art. The preferred technique for measuring this criteria is the use of a wavefront sensor (aberrometer) to obtain real-time wavefront aberration information. The preferred design parameters are physical design parameters such as the shape of the posterior lens surface, the shape of the anterior lens surface, and/or the asphericity of the anterior lens surface. Alternatively, the design parameter may be an optical parameter such as the higher-order aberration content of the lens, e.g., the amount of spherical aberration of the lens. The design parameter may alternatively be in the form of a lens factor that induces a higher-order aberration in the patient's eye. Most preferably, the and described in detail below, and defined in the appended claims, involves making test lens measurements on a statistically significant population group. The preferred design parameter will then coincide with the best objectively measured optical performance determined by statistical analysis. The design method thus allows the lens designer to develop contact lenses that will provide the best optical performance for the largest cross section of contact lens wearers.

Another embodiment according to the invention relates to a method for providing a contact lens that delivers improved in-situ optical performance. An aspect of this embodiment involves the steps of obtaining a subject's manifest refraction and prescribing an appropriate contact lens designed according to the design method set forth herein. In a related aspect, a method is described for fitting an individual with an optimized contact lens. In this method, the subject is fitted with a first trial lens having the appropriate refractive power and a first design parameter value. The optical performance of the test lens is objectively measured in-situ, and the subject is again fitted with a second test lens of the appropriate power having a different value of the respective design parameter. Another measurement is then obtained. This process is repeated as desired, and the lens that provides the optimum optical performance (in consideration of comfort and other factors) can be prescribed and dispensed to the patient.

In another embodiment according to the invention, a method for using an aberrometer for designing and prescribing a contact lens includes making a wavefront measurement of a subject's eye with a first in-situ trial lens having a known design parameter value that affects optical performance, making another wavefront measurement of the subject's eye with another in-situ trial lens having a respective design parameter of a different value, monitoring an objective optical performance metric of each trial lens based upon the respective wavefront measurements, and designing or prescribing a contact lens based upon the design parameter of the trial lens that provided the optimum optical performance metric.

The methods and apparatus according to the invention are embodied in various types and styles of contact lenses including, but not limited to, a soft monofocal lens, a soft multifocal lens, an RGP monofocal lens, an RGP multifocal lens, a toric lens, simultaneous style presbyopia correcting lenses, alternating vision style presbyopia correcting lenses, and diffractive lenses.

The stated objects and advantages of the invention, and others, will be further appreciated in view of the description and drawings that follow, and by the appended claims which define the invention.

DETAILED DESCRIPTION OF PREFERRED EMBODIMENTS OF THE INVENTION

References made herein to the term in-situ mean the trial contact lens being worn by a subject. Higher-order aberrations refer to third and higher order Zernike polynomial representations or their equivalents and will be understood to exclude defocus and cylinder. The term "statistically significant sample" is conventionally understood to represent 30 or more sample eyes.

Figure 1:
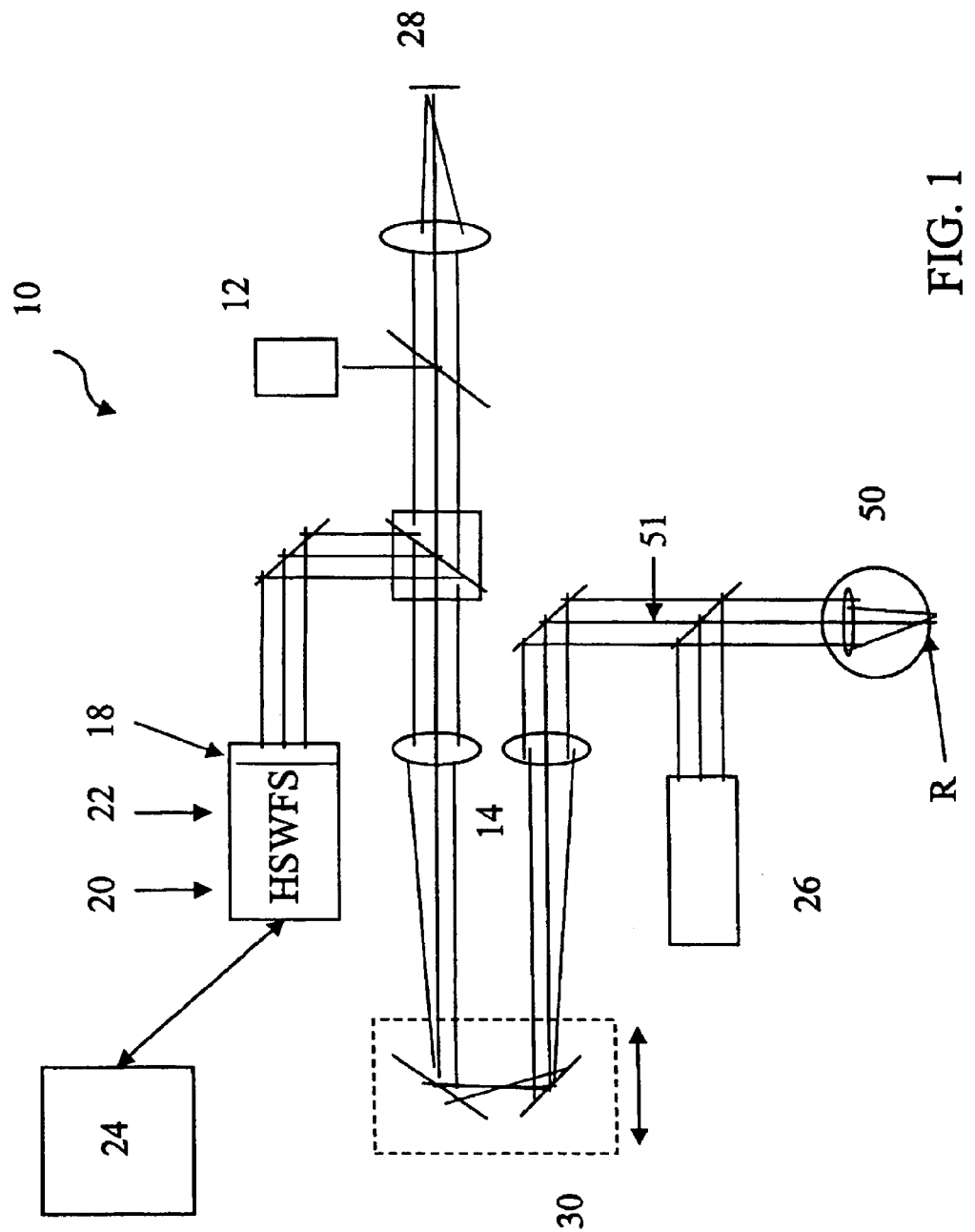
FIG. 1 is an optical schematic of a Shack-Hartmann aberrometer used in conjunction with the invention.

An embodiment of the invention is directed to a method for designing a contact lens. The most general approach initially involves determining or selecting a metric representative of optical performance. A traditional example of such a metric is Snellen visual acuity in which a practitioner (who may present a patient with a series of trial lenses) receives subjective feedback from the patient about how clearly they can read the progressively smaller figures of a Snellen chart. In contrast to this subjective exercise, an optical performance metric according to the invention is an objective measurement of optical performance of a contact lens in-situ. Preferably, this will be a retinal image metric. The Strehl ratio is an example of a preferred retinal image metric. The point spread function (PSF) is a related, non-limiting example of a retinal image metric. Examples of additional metrics include, e.g., modulation transfer function, contrast sensitivity, neural contrast sensitivity, variance of the PSF, encircled energy in the Airy disk of a PSF, and entropy of a PSF. Next, a technique for objectively measuring the optical performance of the contact lens in-situ is determined. The preferable technique according to the invention involves the use of an aberrometer (wavefront sensor device) to determine the Zernike coefficients of the higher-order aberrations and to calculate the retinal image metric of choice. A Shack-Hartmann wavefront sensor is the preferred measurement device, although aberrometers based upon other well known principles such as, but not limited to, Tscheming, skiascopic, sequential scanning, Tracey type, and others, are also suitable. FIG. 1 is an optical schematic of a Shack-Hartmann aberrometer 10 that aids in illustration of an embodiment according to the invention. The aberrometer 10 uses a laser diode 12 to illuminate a subject's eye 50 while the subject fixates on a target 28. A trombone optical system 30 is available to correct defocus errors. Scattered/reflected light from the eye's retina, R, is directed to both a pupil camera 26 to aid in alignment and to a microlens (Oenslet) array 18 that images the reflected light into an array of spots on a sensor 22 associated with a wavefront camera 20. The image spot signals are digitally processed and wavefront aberrations preferably in the form of Zernike coefficients are computed and output, as well understood in the art. In a next step, a lens design parameter is determined that can be varied to induce a change in the optical performance of the lens in-situ. These can take the form of physical lens parameters or optical design parameters. In a preferred aspect, the parameters are physical design variables such as posterior or anterior lens surface shape or anterior surface asphericity. A subsequent step involves measuring the in-situ optical performance of a test lens over a range of different design parameter values. For instance, a subject would be fitted with a test contact lens of the type ultimately to be worn, having the appropriate refracting power (e.g., 3D for defocus correction) and a known anterior surface asphericity. The optical performance of the lens would be objectively evaluated with the aberrometer measurement. Then the subject would be fitted with another test lens of the same refracting power but a different, respective, design parameter value, and the optical performance again measured. These process steps would be repeated for a number of different trial lenses, preferably on a statistically significant sample group, to determine the best lens design for the broadest population segment based on measured in-situ optical performance. The best design need not be limited to a single design but may consist of more than one lens design to cover a larger number of wearers.

Figures 2A, 2B, 2C:
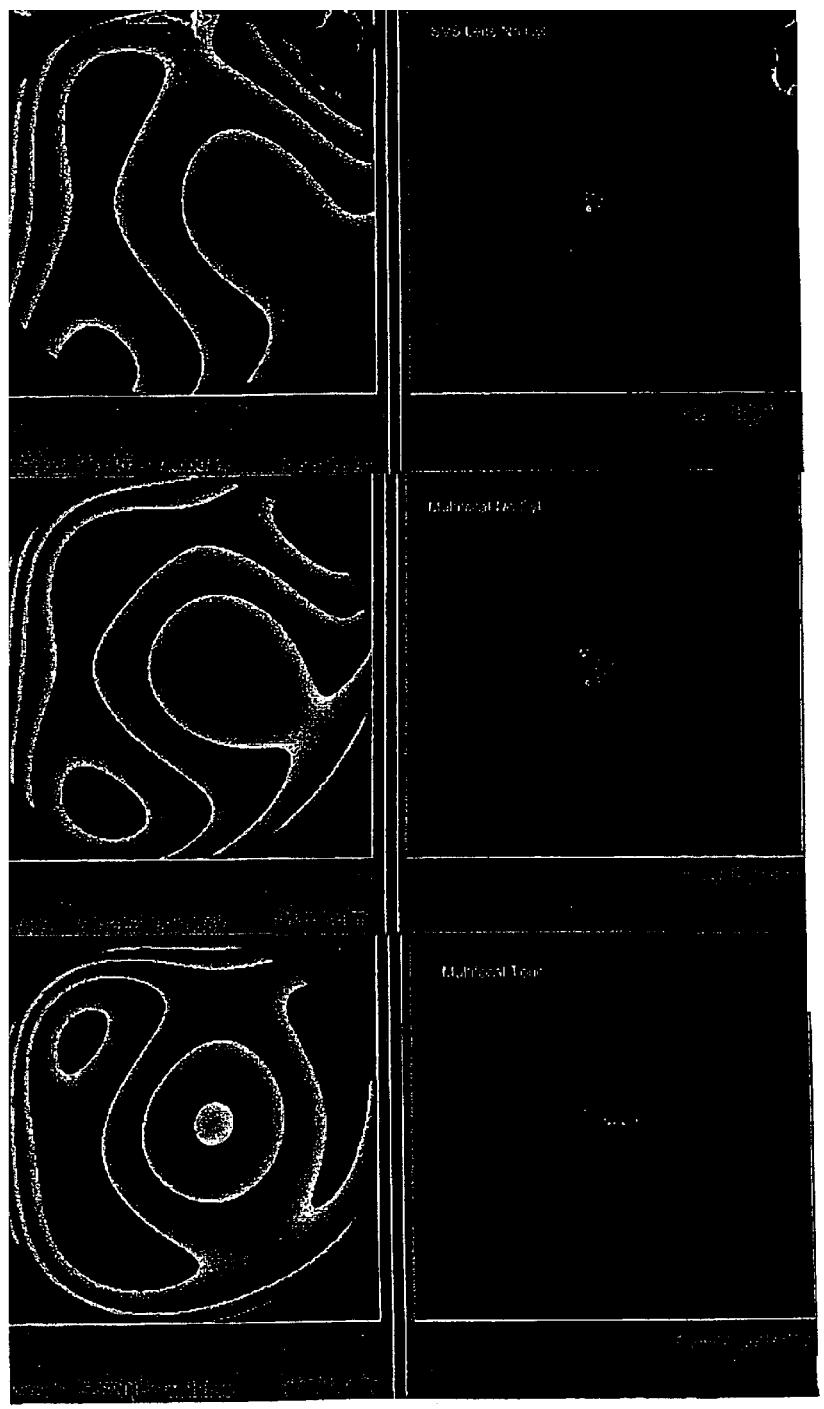
FIGS. 2a–c are a series of wavegrams and associated point spread functions used to illustrate an embodiment of the invention.

FIGS. 2a–c illustrate by example the foregoing embodiment of the invention. The exemplary patient suffers from presbyopia with astigmatism. In FIG. 2(a), a wavefront (wavegram) of the patient's vision is shown, with the patient wearing a single vision spherical contact lens to correct myopia but not the astigmatism. There are $0.14\mu$ of spherical aberration present. The calculated objective vision metric, the Strehl ratio, has a value of 0.03174. In FIG. 2(b), the patient has been fitted with a Unilens® (Unilens Corp., Largo, Fla.) simultaneous style, multi-focal contact lens without astigmatism correction on the same eye as in FIG. 2(a). The Strehl ratio has decreased to 0.01807 while the measured spherical aberration has increased to $0.34\mu$ due to the multi-focal lens design. In spite of the decrease in the vision metric and the increased amount of spherical aberration, the patient's subjective visual performance has improved to a compromise in good far vision and good near vision, still, however, without astigmatism correction. In FIG. 2(c), wavefront sensor measurements have been used to iterate the maximum amount of spherical aberration (0.45 $\mu$) that can be incorporated into the lens by changing the anterior lens surface toric asphericity to correct the astigmatism, thus improving the person's vision even more. In other words, the Strehl ratio increased with the astigmatism correction. The spherical aberration was then increased until the Strehl ratio substantially matched the calculated Strehl ratio prior to the astigmatism correction. The increased spherical aberration advantageously improved the patient's presbyopic near-vision by increasing the patient's depth of field. This process, run iteratively on the eye of a patient, could be applied, in a preferred aspect of this embodiment, to a statistically significant number of patients' eyes to determine the spherical aberration increase that could be put into a toric multi-focal contact lens for commercial distribution. It will be appreciated that once a satisfactory non-astigmatism-correcting multi-focal lens has been fitted on the patient and the desired image quality metric determined, the iterative optimization of the lens for astigmatic correction can be performed on a single patient's eye or, preferably, on a statistically significant number of eyes. Moreover, monitoring of the image quality metric and the aberration content (e.g., spherical aberration) as a function of lens surface parameters can preferably be done by simulation using the aberrometer data, without having to actually iteratively fit lenses to the patient's eye.

In another embodiment according to the invention, a method for prescribing a contact lens comprises using a plurality of real-time wavefront measurements of the in-situ optical performance of a respective plurality of trial contact lenses as a function of a physical design parameter to determine the best in-situ optical performance for a statistically significant sample of subjects, and prescribing the contact lens that is similar to the best performing trial lens. In a preferred aspect of this embodiment, a practitioner will have access to one or more lenses for each lens power that have been designed as described according to the invention.

In other words, the trial fittings on a subject will be of trial lenses that have been designed to provide the best optical performance for the largest cross sections of wearers or for the most number of people. Of course, the lens designs are based upon statistical performance data; therefore, custom lenses may be available on an individual type basis that actually provide optimum optical performance.

In practice, a method for prescribing a contact lens would include the steps of providing a plurality of trial lenses to a subject, each of which provides a desired correction for sphere and cylinder and wherein each of the trial lenses has a different, respective, design parameter; fitting each trial lens on the subject; obtaining a real-time wavefront measurement of the in-situ optical performance of each lens as measured by an objective retinal image metric; and prescribing a contact lens for the subject in accord with the best measured optical performance of the trial lenses.

The following clinical observations additionally illustrate the foregoing described embodiments of the invention. Fifteen (15) subjects (adapted pre-presbyopic subjects, all habitual soft contact lens wearers) were enrolled in an insertion study to compare the clinical fitting performance and efficacy of the Zywave™ wavefront sensor (Bausch & Lomb. Inc., Rochester, N.Y.) on three castmolded bifocal shape factor lenses and one Unilens EMA Multifocal lens. Subjects with spectacle refractions between −2.00D to −4.50D and with less than −0.75D of corneal astigmatism in one eye were selected. The study demonstrated the efficacy of the Zywave wavefront sensor in differentiating the on-eye wavefront changes induced by soft contact lenses designed with several levels of spherical aberration. The study results showed that a wavefront sensor is a useful instrument in measuring the on-eye performance changes resulting from the design alteration of multifocal lenses for the study. Test lenses were made with PVC/PVC molds and HEMA B IMVT monomer. The three iterations differed only in the posterior tool shape factor. All test lenses were −3.00D with a "Low Add" anterior surface. Nominal parameters were as follows in Table 1. The control lenses were Unilens EMA Multifocal lenses, −3.00D/8.8 Base Curve/Low Add.

TABLE 1

Lens Parameters

| Posterior Tool Shape Factor | Avg. Diameter (mm) | Avg. Sag (mm) | Avg. Center Thickness (mm) | Avg. EBC (mm) | Avg. Edge Thickness (mm) |
|---|---|---|---|---|---|
| 0.80 | 14.45 | 3.71 | 0.081 | 9.00 | 0.076 |
| 1.00 | 14.43 | 3.72 | 0.084 | 8.98 | 0.075 |
| 1.20 | 14.44 | 3.71 | 0.082 | 9.00 | 0.076 |

Figure 4:
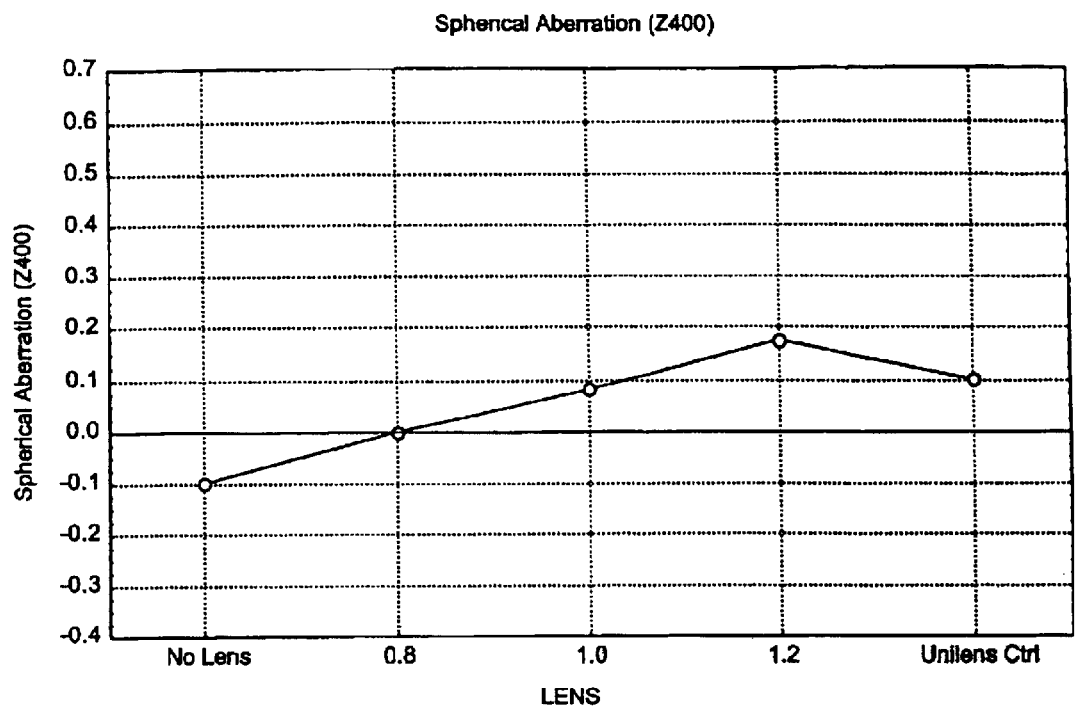
FIG. 4 is a graph showing fourth-order spherical aberration values for several data sites having different design parameters.
Figure 3:
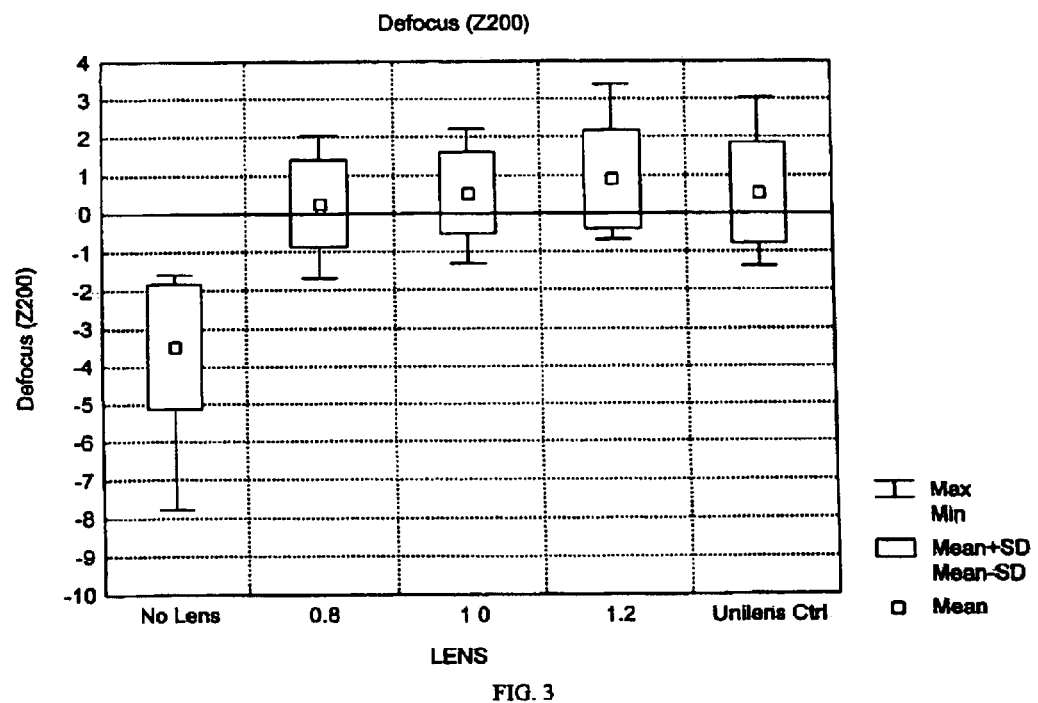
FIG. 3 is a chart showing a range of measured defocus values for several data sites having different design parameters.

In one visit, subjects wore four lenses for a period of no longer than 15 minutes. One eye of each subject was randomly selected as the test eye, lenses were inserted in random, successive order. The subjects were masked to the lens identity. Prior to lens insertion corneal staining was assessed with a slitlamp. Three baseline Zywave wavefront measurements were taken with no lens on the selected eye. A study lens was then inserted into the selected eye of the patient and allowed to settle. Three Zywave measurements were repeated through the lens. Nasal, temporal and inferior lens limbal overlap was measured. Testing was repeated in the same order on the remaining three lenses. Unless otherwise noted, a one-way ANOVA was used to test for differences in each of the parametric dependent variables measured. Differences at the p=0.05 level were considered to be statistically significant. The descriptive data are summarized in Table 2 below. There was no statistically significant difference between the lenses for movement or centration (p>0.08 in all cases). There were no statistically significant differences between the lenses for vertical astigmatism (p=1.00,), for horizontal astigmatism (p=0.99,), for vertical coma (p=Q.96,), for horizontal coma (p=0.64,), for vertical trefoil (p=0.93,), or for horizontal trefoil (p=0.99). A statistically significant difference was found between the lenses for defocus (p<0.001), as shown in FIG. 3. The No Lens measurement condition showed significantly more negative defocus than the four lenses (p=0.0001, Tukey's HSD test). A trend toward increased positive defocus was seen as the posterior shape factor increased from 0.8 to 1.2. This trend is likely due to the design of the lenses such that increasing minus power from the center of the lenses to the periphery results in more positive defocus as the posterior shape factor increases from 0.8 to 1.2. A statistically significant difference was found for spherical aberration between the lenses (p=0.003), as shown in FIG. 4. The No-Lens case was significantly different from the 1.0, 1.2 and Unilens control lenses (p<0.031, Tukey's HSD test), and the 0.8 lens was significantly different from the 1.2 lens (p<0.039, Tukey's HSD test). Overall, there was a trend toward increased overcorrected spherical aberration (more minus in lens periphery) from No-Lens to the 1.2 shape factor lens (i.e. an increase in overcorrected spherical aberration was seen as the posterior shape factor increased). There were no statistically significant differences between the lenses for Zernikes 420–550 (p<0.926 in all cases).

TABLE 2

Descriptive Statistics

|  | Valid N | Mean | Minimum | Maximum | Std. Dev. |
|---|---|---|---|---|---|
| Movement Low | 15 | 0.460 | 0.200 | 1.000 | 0.210 |
| Movement Medium | 15 | 0.393 | 0.200 | 0.800 | 0.175 |
| Movement High | 15 | 0.447 | 0.200 | 1.000 | 0.192 |
| Movement Unilens | 15 | 0.527 | 0.100 | 1.800 | 0.383 |
| Inferior Overlap Low | 15 | 1.933 | 1.500 | 2.400 | 0.272 |
| Inferior Overlap Medium | 15 | 1.920 | 1.500 | 2.200 | 0.227 |
| Inferior Overlap High | 15 | 1.947 | 1.400 | 2.800 | 0.331 |
| Inferior Overlap Unilens | 15 | 1.993 | 1.500 | 2.400 | 0.255 |
| Horizontal Decentration Low | 15 | 0.173 | 0.000 | 0.500 | 0.131 |
| Horizontal Decentration Medium | 15 | 0.180 | 0.000 | 0.600 | 0.160 |
| Horizontal Decentration High | 15 | 0.233 | 0.000 | 0.650 | 0.159 |
| Horizontal Decentration Unilens | 15 | 0.157 | 0.000 | 0.450 | 0.137 |

Low = 0.8 shape factor
Medium = 1.0 shape factor
High = 1.2 shape factor

While various advantageous embodiments have been chosen to illustrate the invention, it will be understood by those skilled in the art that changes and modifications can be made therein without departing from the scope of the invention as defined in the appended claims.

We claim:

1. A contact lens having a physical design parameter determined by an objective wavefront measurement of a plurality of in-situ trial contact lenses each having a different value of the physical design parameter for a given correcting power.

2. The contact lens of claim 1, wherein the contact lens is one of a soft monofocal lens, a soft multifocal lens, an RGP monofocal lens, an RGP multifocal lens, a toric lens, a simultaneous style presbyopia correcting lens, an alternating vision style presbyopia correcting lens, and a diffractive lens.

3. The contact lens of claim 1, wherein one of a PSF and a Strehl ratio are used to determine an improved in-situ optical performance is by the lens.

4. The contact lens of claim 1, wherein the design parameter is at least one of the shape of the posterior lens surface, the shape of the anterior lens surface, and the asphericity of the anterior lens surface.

5. A method for designing a contact lens, comprising:
   a) determining an objective measurement criteria of optical performance of a contact lens in-situ;
   b) determining a technique for measuring this criteria;
   c) determining a lens design parameter that can be varied to induce a change in the optical performance of the lens in-situ;
   d) measuring the in-situ optical performance of a test lens over a range of different design parameter values; and;
   e) selecting the design parameter value for designing a contact lens that gives a desired in-situ optical performance measurement.

6. The method of claim 5, wherein determining the objective, in-situ optical performance further comprises determining a retinal image metric including at least one of the PSF and the Strehl ratio.

7. The method of claim 5, comprising using a wavefront sensor for measuring the optical performance criteria.

8. The method of claim 5, wherein determining the lens design parameters further comprises determining at least one of the shape of the posterior lens surface, the shape of the anterior lens surface, and the asphericity of the anterior lens surface.

9. The method of claim 5, wherein determining the lens design parameters further comprises determining an optical design parameter including the higher-order aberration content of the lens.

10. The method of claim 9, comprising determining an amount of spherical aberration of the lens.

11. The method of claim 5, wherein the lens design parameter is a lens factor that induces a higher-order aberration in the patient's eye.

12. The method of claim 5, wherein measuring the in-situ optical performance of a test lens involves making test lens measurements on a statistically significant population group.

13. A method for designing a contact lens, comprising:
   a) selecting a plurality of trial contact lenses each of which has a substantially similar refracting power and a different, respective, design parameter;
   b) obtaining a real-time wavefront measurement of the in-situ optical performance of each trial contact lens;
   c) monitoring the different design parameter values of the lenses in conjunction with each optical performance measurement;
   d) using the measure of the in-situ optical performance of the lens design to determine a preferred design parameter value; and
   e) designing a contact lens based upon the preferred design parameter value.

14. The method of claim 13, wherein obtaining a real-time wavefront measurement comprises measuring each lens on a statistically significant population group.

15. The method of claim 13, wherein obtaining a real-time wavefront measurement of the in-situ optical performance further comprises determining a retinal image metric including at least one of the PSF and the Strehl ratio.

16. The method of claim 13, wherein selecting different, respective, design parameters includes selecting at least one of the shape of the posterior lens surface, the shape of the anterior lens surface, and the asphericity of the anterior lens surface.

17. An improved method for prescribing a contact lens, comprising using a plurality of real-time wavefront measurements of the in-situ optical performance of a respective plurality of trial contact lenses as a function of a physical design parameter to determine the best in-situ optical performance for a statistically significant sample of subjects.

18. An improved method for prescribing a contact lens, comprising:
   a) providing a plurality of trial lenses each of which provides a desired correction for sphere and cylinder, wherein each of the trial lenses has a different, respective, design parameter;
   b) consecutively providing each trial lens to a subject in-situ;
   c) obtaining a real-time wavefront measurement of the in-situ optical performance of each lens; and
   d) prescribing a contact lens for the subject in accord with the best measured optical performance of the trial lenses.

19. An improved method for providing a contact lens, comprising:
   a) obtaining a refraction measurement of a subject's eye;
   b) selecting a plurality of trial contact lenses each of which have a similar refractive correction power and a different, respective, design parameter;
   c) applying a first one of the trial contact lenses on the subject's eye;
   d) obtaining a wavefront measurement of the in-situ optical performance of the first one trial contact lens;
   e) removing said trial contact lens and applying a different, next one of the trial contact lenses on the subject's eye;
   f) obtaining a wavefront measurement of the in-situ optical performance of the next trial contact lens;
   g) repeating steps (e) and (f) for a desired number of trial lenses; and
   h) providing a contact lens similar to the trial lens that provides the optimum optical performance in-situ.

20. The method of claim 19, wherein the design parameter is at least one of the shape of the posterior lens surface, the shape of the anterior lens surface, and the asphericity of the anterior lens surface.

21. The method of claim 19, wherein the design parameter is a higher-order aberration content of the lens.

22. The method of claim 21, wherein the design parameter is the amount of spherical aberration of the lens.

23. The method of claim 19, wherein the design parameter is a lens factor that induces a higher-order aberration in the patient's eye.

24. The method of claim 22, wherein the lens factor induces an amount of spherical aberration in the patient's eye.

25. The method of claim 19, wherein the prescribed contact lens is one of a soft monofocal lens, a soft multifocal lens, an RGP monofocal lens, an RGP multifocal lens, and a toric lens.

26. A method for using an aberrometer for designing and/or prescribing a contact lens, comprising:
   making a wavefront measurement of a subject's eye with a first in-situ trial lens having a known design parameter value that affects optical performance;

making a next wavefront measurement of a subject's eye with a next in-situ trial lens having a different valued, respective, known design parameter that affects optical performance;

determining an objective optical performance metric of each trial lens based upon the respective wavefront measurement; and designing and/or prescribing a contact lens based upon the design parameter of the trial lens that provided the optimum optical performance metric.

27. The method of claim 26, wherein making a wavefront measurement further comprises determining a retinal image metric including at least one of the PSF and the Strehl ratio.

28. The method of claim 26, wherein the known lens design parameters comprise at least one of the shape of the posterior lens surface, the shape of the anterior lens surface, and the asphericity of the anterior lens surface.

29. The method of claim 26, comprising using a Shack-Hartmann aberrometer to make the wavefront measurements.

30. A method for designing a contact lens, comprising the steps of:

a) providing a simultaneous style multi-focal trial contact lens to a patient having astigmatic presbyopia such that the trial lens provides a subjectively determined satisfactory visual quality for near-vision and far-vision defocus without an astigmatic correction;

b) measuring a wavefront aberration of the in-situ placement of the trial lens and determining an objective vision quality metric corresponding to the subjectively determined visual quality; and c) changing a design parameter of the trial lens to reduce the astigmatism aberration and so changing a spherical aberration of the wavefront measurement until a value of an associated objective vision quality metric becomes substantially the same as the determined objective vision quality metric.

31. The method of claim 30, wherein determining an objective vision quality metric includes determining an image plane metric comprising at least one of a PSF, an MTF, a Strehl ratio, a neural contrast sensitivity function, a contrast sensitivity function, a variance of a PSF, an entropy of a PSF, and an encircled energy within an Airy disk of a PSF.

32. The method of claim 30, wherein changing a design parameter of the trial lens to reduce the astigmatism includes changing an anterior surface shape of the trial lens to produce a toric asphericity on the surface.

33. The method of claim 30, wherein changing a design parameter of the trial lens to reduce the astigmatism aberration comprises monitoring the wavefront aberrations and reducing the Zernike coefficient associated with the astigmatism.

34. The method of claim 30, wherein step (c) involves a simulated change using an aberrometer measurement and associated aberration and image quality metric calculations provided the aberrometer.

* * * * *

UNITED STATES PATENT AND TRADEMARK OFFICE
CERTIFICATE OF CORRECTION

PATENT NO. : 6,802,605 B2 Page 1 of 1
DATED : October 12, 2004
INVENTOR(S) : Ian Cox et al.

It is certified that error appears in the above-identified patent and that said Letters Patent is hereby corrected as shown below:

Column 10,
Line 28, insert -- by -- after the word "provided" and before "the".

Signed and Sealed this

Nineteenth Day of July, 2005

JON W. DUDAS
*Director of the United States Patent and Trademark Office*